(12) United States Patent
Graf

(10) Patent No.: US 7,727,258 B2
(45) Date of Patent: Jun. 1, 2010

(54) INTERVERTEBRAL STABILIZING DEVICE

(75) Inventor: Henry Graf, Lyons (FR)

(73) Assignee: Warsaw Orthopedic, Inc.

( * ) Notice: Subject to any disclaimer, the term of this patent is extended or adjusted under 35 U.S.C. 154(b) by 971 days.

(21) Appl. No.: 10/433,211

(22) PCT Filed: Nov. 30, 2001

(86) PCT No.: PCT/FR01/03804

§ 371 (c)(1),
(2), (4) Date: Jan. 13, 2004

(87) PCT Pub. No.: WO02/43603

PCT Pub. Date: Jun. 6, 2002

(65) Prior Publication Data

US 2004/0116927 A1 Jun. 17, 2004

(30) Foreign Application Priority Data

Dec. 1, 2000 (FR) .................................. 00 15621

(51) Int. Cl.
*A61B 17/70* (2006.01)
(52) U.S. Cl. ..................................... 606/253
(58) Field of Classification Search ... 623/17.11–17.16; 606/60, 61
See application file for complete search history.

(56) References Cited

U.S. PATENT DOCUMENTS

| | | | |
|---|---|---|---|
| 3,316,558 A | 5/1967 | Mortensen | |
| 3,648,294 A | 3/1972 | Shahrestani | |
| 3,853,311 A | 12/1974 | Kreuger et al. | |
| 4,066,279 A | 1/1978 | Kaptanis | |
| 4,458,888 A | 7/1984 | Wolf et al. | |
| 4,504,044 A | 3/1985 | Shtarkman | |
| 4,509,730 A | 4/1985 | Shtarkman | |
| 4,830,346 A | 5/1989 | Eberhard et al. | |
| 4,932,969 A | 6/1990 | Frey et al. | |
| 5,295,563 A | 3/1994 | Bennett | |
| 5,342,361 A * | 8/1994 | Yuan et al. | 606/61 |
| 5,375,823 A | 12/1994 | Navas | |
| 5,376,138 A | 12/1994 | Bouchard et al. | |
| 5,458,642 A | 10/1995 | Beer et al. | |
| 5,460,355 A | 10/1995 | Danek | |
| 5,466,261 A | 11/1995 | Richelsoph | |
| 5,480,401 A | 1/1996 | Navas | |
| 5,540,688 A | 7/1996 | Navas | |

(Continued)

FOREIGN PATENT DOCUMENTS

EP 0 277 282 A1 10/1987

(Continued)

*Primary Examiner*—Anu Ramana

(57) ABSTRACT

The present invention is related to an intervertebral stabilizing device structured to connect two adjacent vertebrae. The device includes an upper stop element engageable with an upper vertebra and a lower stop element engageable with a lower vertebra. The stop elements include mutual support surfaces adapted to allow a mutual rotation of the upper and lower vertebrae about the patient's transverse and sagittal axes and to prevent a mutual rotation of the two vertebrae about a vertical axis. The support surfaces are further adapted to allow mutual translation of the vertebrae in a single direction along the sagittal axis and to allow translation between the two vertebrae in both directions along a vertical axis. Additionally, the support surfaces are also adapted to prevent translation between the two vertebrae in both directions along the transverse axis.

11 Claims, 3 Drawing Sheets

U.S. PATENT DOCUMENTS

| | | |
|---|---|---|
| 5,562,737 A | 10/1996 | Graf |
| 5,571,191 A | 11/1996 | Fitz |
| 5,702,450 A | 12/1997 | Bisserie |
| 5,775,677 A | 7/1998 | Englund |
| 5,860,973 A | 1/1999 | Michelson |
| 5,961,516 A | 10/1999 | Graf |
| 6,063,121 A | 5/2000 | Xavier et al. |
| 6,082,508 A | 7/2000 | Davis |
| 6,146,421 A | 11/2000 | Gordon et al. |
| 6,179,874 B1 | 1/2001 | Cauthen |
| 6,228,118 B1 | 5/2001 | Gordon |
| 6,248,106 B1 * | 6/2001 | Ferree .................. 606/61 |
| 6,322,059 B1 | 11/2001 | Kelm et al. |
| 6,419,706 B1 | 7/2002 | Graf |
| 6,692,495 B1 | 2/2004 | Zacouto |
| 6,835,207 B2 | 12/2004 | Zacouto et al. |
| 2002/0151978 A1 | 10/2002 | Zacouto et al. |
| 2003/0055427 A1 | 3/2003 | Graf |

FOREIGN PATENT DOCUMENTS

| | | |
|---|---|---|
| EP | 0 282 161 A1 | 9/1988 |
| EP | 0 820 731 A2 | 1/1998 |
| EP | 0 953 317 A1 | 11/1999 |
| FR | 2 676 911 A1 | 12/1992 |
| FR | 2 723 841 A1 | 8/1994 |
| FR | 2 744 010 | 8/1997 |
| GB | 1 306 660 | 2/1973 |
| JP | 07008504 A2 | 1/1995 |
| JP | 10-277070 A2 | 10/1998 |
| JP | 11502437 | 3/1999 |
| JP | 2003/515381 A | 5/2003 |
| WO | WO 97/35529 A1 | 10/1997 |
| WO | WO 01/30248 A1 | 5/2001 |
| WO | WO 01/39678 A1 | 6/2001 |
| WO | WO 01/49192 A1 | 7/2001 |
| WO | WO 02/43603 A1 | 6/2002 |

* cited by examiner

INTERVERTEBRAL STABILIZING DEVICE

BACKGROUND

The present invention concerns an intervertebral stabilizing device.

SUMMARY

The present invention provides a device which makes it possible to restore the stability between two adjacent vertebrae when the posterior intervertebral articulation has been totally or partially destroyed because of surgery or a disease.

To this end, the intervertebral stabilizing device is structured to connect two adjacent vertebrae and includes an upper stop element engageable with an upper vertebra and a lower stop element engageable with a lower vertebra. The stop elements include mutual support surfaces adapted to allow mutual rotation of the upper and lower vertebrae around the transverse and sagittal axes of a patient as well as to prevent mutual rotation of these two vertebrae around a vertical axis. In addition, these support surfaces are adapted to allow mutual translation of these vertebrae in a single direction along the sagittal axis and to allow translation between these two vertebrae in both directions along the vertical axis. Moreover, the support surfaces are configured to prevent translation between these two vertebrae in both directions along the transverse axis.

Other forms of the present invention may include various features. For example, one of the stop elements may include two flat support surfaces arranged on both sides of the vertical axis, these two surfaces extending obliquely and interacting with two spheres arranged on two support surfaces of the other of said stop elements.

In another form the device comprises at least one upper pedicular screw and at least one lower pedicular screw with each stop element being engageable with at least one of said pedicular screws.

In yet another form, each stop element is engageable with both of the upper and lower pedicular screws, respectively.

In still another form, means are provided for transversely adjusting the position of each stop element, which in one form may be provided by an oblong opening in each of the stop elements.

In yet another form, means are provided for selectively interlocking each stop element in translation with at least one pedicular screw.

In still another form, the device comprises an extra-discal member arranged at the back of the intervertebral space which is structured for absorbing displacement between the vertebrae at least in the direction of intervertebral flexion.

In an additional form, the device comprises at least one intersomatic implant structured to be inserted at least partially between the vertebral bodies of the two neighboring vertebrae.

DETAILED DESCRIPTION OF THE PREFERRED EMBODIMENTS

Figure 1:
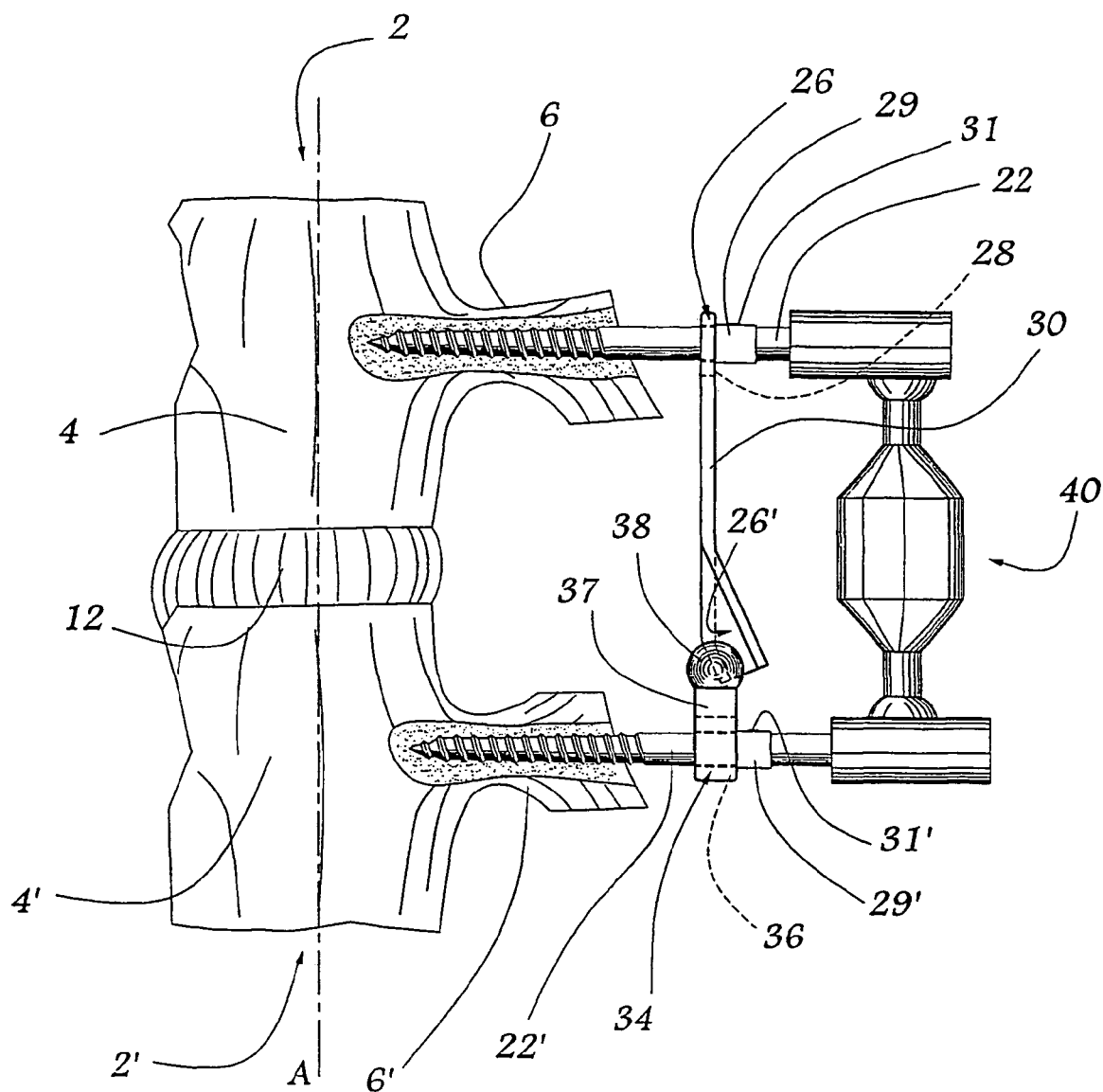
FIG. 1 is a lateral diagrammatic view illustrating two adjacent vertebrae between which is placed a stabilizing device in conformance with the invention.

FIG. 1 represents two vertebrae, upper 2 and lower 2', respectively, which are connected through a stabilizing device in accordance with the present invention. Each vertebra includes a vertebral body 4, 4' which is respectively extended by a pedicle 6, 6'. An intervertebral space 12 is formed between the vertebral bodies 4, 4'. Note that the patient has undergone removal of the major part of his posterior intervertebral articulation.

Figure 2:
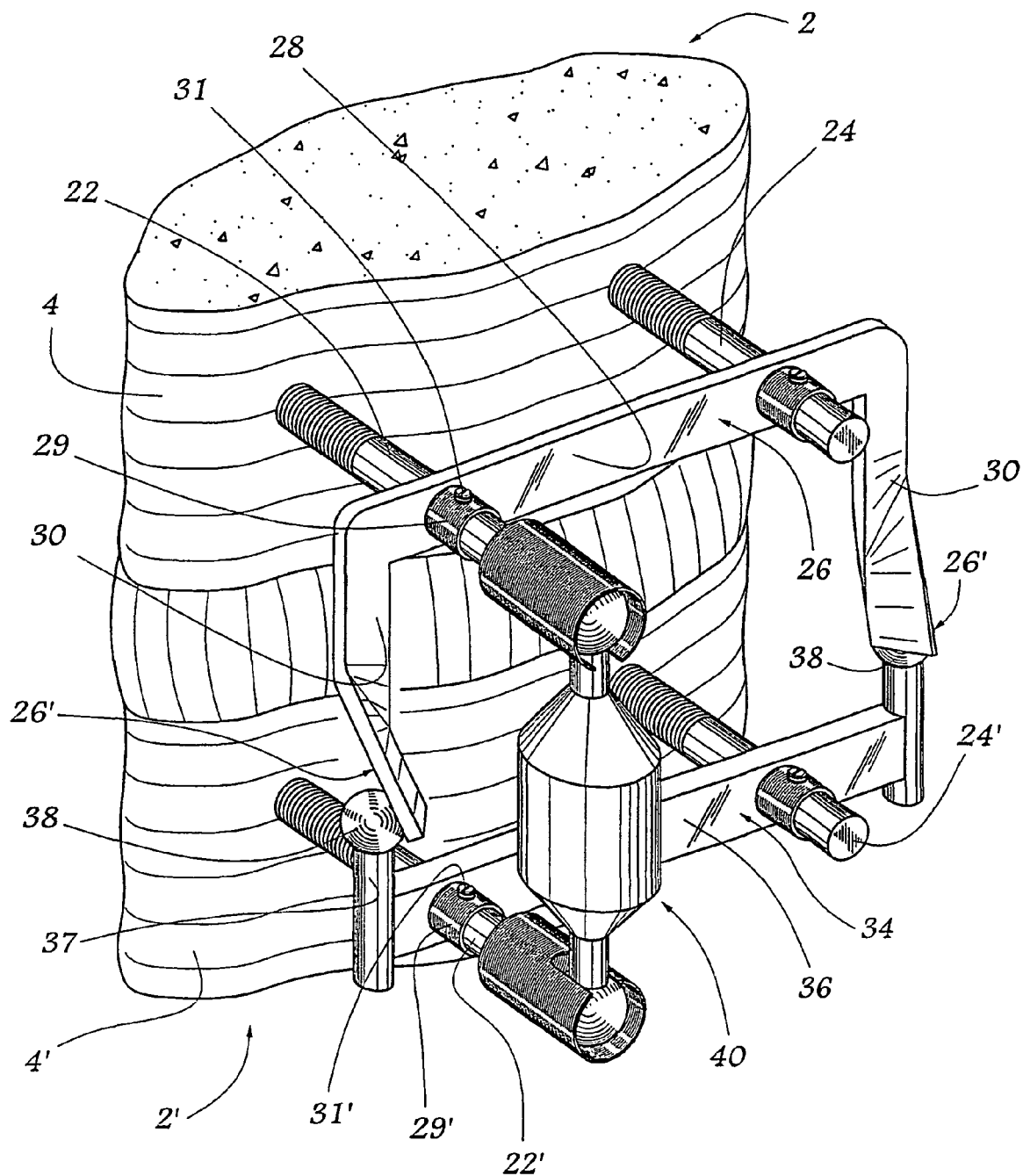
FIG. 2 is a perspective view illustrating the device of FIG. 1.

As is shown more specifically in FIG. 2, the upper vertebra includes two upper pedicular screws 22, 24 engaged therewith and arranged on both sides of the principal axis of the vertebral column. Moreover, two lower pedicular screws 22', 24', are engaged with the lower vertebra and are arranged approximately below the upper pedicular screws.

The stabilizing device of the invention comprises an upper stop element 26 including a horizontal branch 28 as well as two vertical branches 30. The horizontal branch 28 has two circular holes made in it that are designed for the passage of the shaft of the upper pedicular screws 22, 24. The walls of each opening are extended by an axial sheath 29 which covers part of the screw. The sheath 29, which may be derived from the same material as branch 28, receives a clamping screw 31 adapted to immobilize the stop element selectively in relation to the pedicular screw along a translation parallel to the principal axis of the latter.

This device also includes a lower stop element 34 including a horizontal branch 36 extended at its ends by rods 37 which include spheres 38. This lower element 34 has two openings made in it that are designed for the passage of the shaft of the two lower pedicular screws 22', 24'. Similarly to the upper element 26, each opening is provided with an axial sheath 29' which includes a screw 31' adapted to immobilize the stop element 34 selectively in relation to the pedicular screw 22', 24' along a translation parallel to the principal axis of the latter.

Moreover, as a variant, at least one of the openings may be oblong in shape. This oblong shape makes it possible to transversely position the stop elements relative to the pedicular screws. The horizontal branches 28 and 36 may also have variable lengths, and may be in one form, telescopic.

Figure 3:
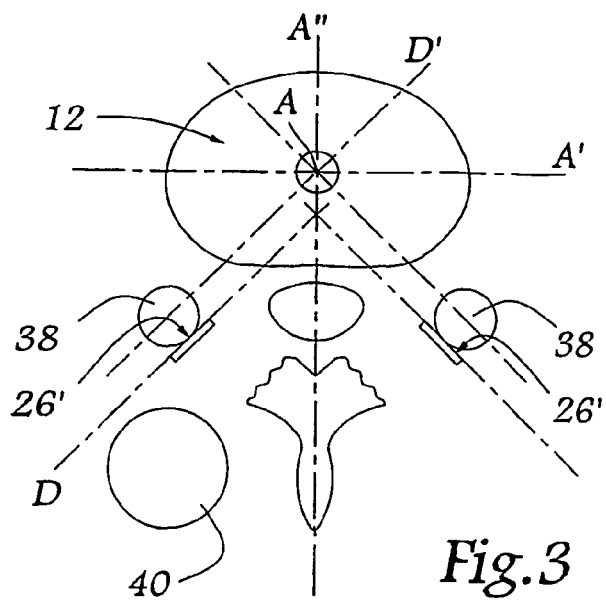
FIGS. 3 to 5 are top views illustrating the device of FIG. 1, as well as two alternative embodiments.

Each vertical branch 30 is folded, such that its end has a flat surface 26' extending obliquely to the upper stop branch 26. Specifically, this oblique direction is neither parallel to the median transverse axis A', extending from the right to the left of the patient, nor parallel to the median sagittal axis A", extending from back to front of the patient (FIG. 3). The principal axis D of this flat surface 26' is parallel to a line D' passing through the intersection of these two axes A' and A", and may be a bisector of these latter axes.

Each support surface 26' interacts or engages with a corresponding sphere 38 positioned at the ends of the rods 37. In this manner, two rotations around axes A' and A" are allowed between the upper and lower stop elements and, consequently, between the two vertebrae 2 and 2'. On the other hand, rotation around the vertical axis A between these two vertebrae is prevented.

Moreover, mutual translation of the two vertebrae 2, 2' along the sagittal axis A" is allowed in a single direction. Thus, the upper vertebra 2 may not be displaced toward the front relative to the lower vertebra 2', but at the same time, is free to be displaced toward the back relative to the lower vertebra 2'.

In addition, any mutual translation of the two vertebrae 2, 2' is prevented in both directions along the transverse axis A'.

Lastly, mutual translation between these two vertebrae is allowed in both directions along the vertical axis A.

Figure 4:
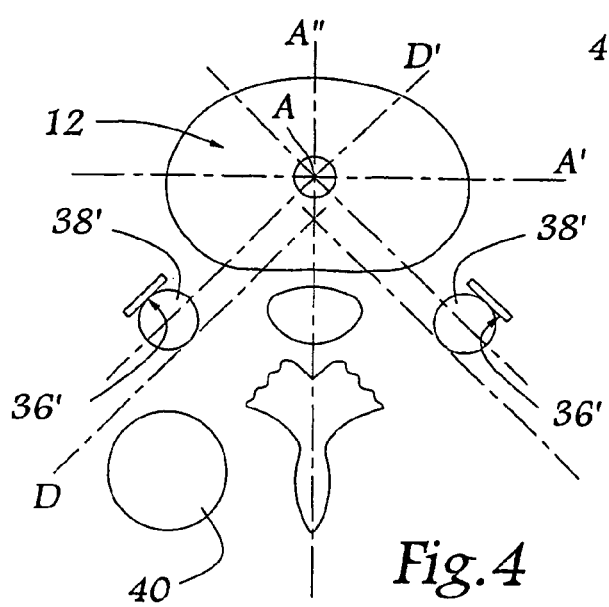
Figure 5:
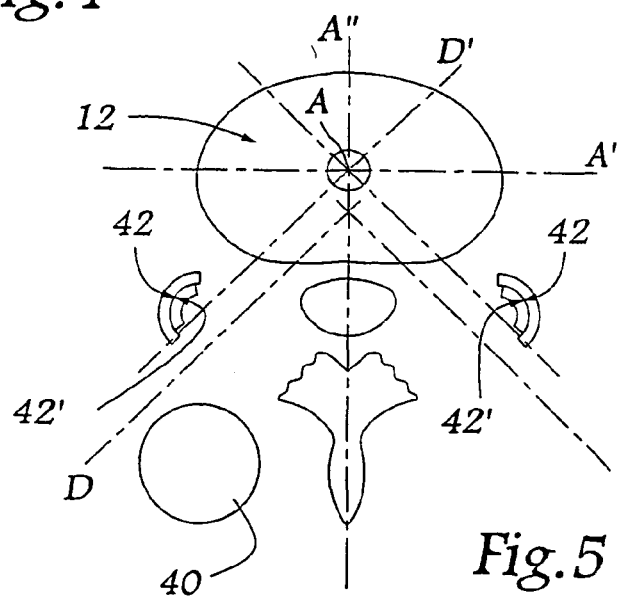

Other embodiments are also contemplated. For example, the upper stop element may be provided with at least one sphere 38' which interacts or engages with a vertical branch terminated by an oblique flat surface 36' extending from the horizontal branch 36 of the lower element (FIG. 4). In another form, the vertical branches 30 and the rods 37 may include adjacent spherical support surfaces 42, 42', which interact or engage with each other as illustrated in FIG. 5.

In an alternative embodiment, at least one of the vertical branches 30 may be made, at least partially, from an elastic material. In this form, the elasticity allows permanent contact between each branch 30 and a corresponding sphere 38. It is also contemplated to make at least one vertical branch from two parts, having a certain mutual displacement in rotation around the principal axis of the branch. In this form, the displacement may be temporary to facilitate positioning two stop elements, or may be permanent to ensure constant angular adaptation between the branch and the sphere.

Moreover, it is contemplated to provide a single vertical branch 30 which interacts or engages with a single sphere 38. In one form, this embodiment may be particularly suited for implantation where part of the natural posterior articulation has not been destroyed.

Moreover, the two adjacent vertebrae 2, 2' are connected by means of an absorbing member 40 which is attached to the two free ends of the pedicular screws 22 and 22'. The absorbing member 40 may be, for example, one of such devices disclosed by FR-A-2 676 911 or even that of FR-A-2 751 864. It may also include a ligament in conformance for example with the disclosure of FR-A-2 694 182.

The absorbing member is structured for absorbing a displacement between the two adjacent vertebrae at least in the direction of intervertebral flexion in which the patient leans forward toward the front.

The invention is not limited to the examples described and represented herein.

For example, it may also be structured for housing an intersomatic implant, which may be partially or totally positioned in the intervertebral space 12. In the case where it is a partial implant, several implants of this type may be arranged between the same two vertebrae.

It is contemplated that the device of the present invention may be put in position either by the anterior route or by the posterior route, by screwing or even by impaction.

In the case of degenerative pathology of the intervertebral disk which extends to the nerves that are adjacent to it, it is necessary for the surgeon to free the compressed nerve root. To that end, the corresponding operation induces at least partial destruction of the posterior intervertebral articulation.

The device of the invention to a great extent makes it possible to restore the posterior stability which had appreciably decreased because of a surgery. In addition, it allows relative movement between the two neighboring vertebrae that is very close to natural movement. In this regard, combining two extra-discal stop elements with an extra-discal absorbing member is quite advantageous.

In one embodiment, wherein each upper or lower element is mounted on two pedicular screws it prevents these screws from being disconnected relative to the vertebral bodies with which they engage. In fact, in this form, the pedicular screws are not subjected to any rotation around their principal axis.

The invention claimed is:

1. An intervertebral stabilizing device, comprising:
    a first stop element engageable with a first vertebra, said first stop element including laterally spaced first and second branches extending in a first direction therefrom, each of said first and second branches having first and second linear portions that are substantially parallel to each other;
    a second stop element engageable with a second vertebra, said second stop element including laterally spaced third and fourth branches extending in a second direction therefrom, each of said third and fourth branches having third and fourth linear portions that are substantially parallel to each other, said third and fourth branches of said second stop element being engageable with said first and second branches of said first stop element;
    wherein each of said first and second branches of said first stop element is positioned laterally relative to a portion of said third and fourth branches of said second stop element; and
    wherein each of said first and second stop elements includes a horizontal branch extending between and laterally spacing the first and second branches and third and fourth branches, respectively.

2. The device of claim 1, wherein each of said third and fourth branches of said second stop element is positioned between the first and second branches of said first stop element.

3. The device of claim 2, wherein each of said first and second branches of said first stop element includes a spherical portion disposed at an end thereof opposite from said horizontal branch.

4. The device of claim 3, wherein each of said third and fourth branches of said second stop element includes a flattened portion disposed at an end thereof opposite from said horizontal branch, said flattened portions extending obliquely to said second stop element and being engageable with said spherical portions of said first and second branches of said first stop element.

5. The device of claim 2, wherein each of said first and second stop elements includes at least one opening extending therethrough sized and structured to receive a pedicular screw.

6. The device of claim 5, wherein at least one of said openings includes an axial sheath extending therefrom, said sheath including a transversely oriented locking element structured to selectively control the positioning of a pedicular screw relative to said first and second stop elements.

7. An intervertebral stabilizing device, comprising:
    a first stop element engageable with a first vertebra, said first stop element including laterally spaced first and second branches extending therefrom, each of said first and second branches having first and second linear portions that are substantially parallel to each other;
    a second stop element engageable with a second vertebra, said second stop element including laterally spaced third and fourth branches extending therefrom, each of said third and fourth branches having third and fourth linear portions that are substantially parallel to each other, said third and fourth branches of said second stop element being positionable in engagement with said first and second branches of said first stop element; and
    wherein said engagement between said first and second branches of said first stop element and said third and fourth branches of said second stop element provides means for facilitating rotation of said first and second vertebrae about transverse and sagittal axes of a patient and means for prohibiting rotation of said first and second vertebrae about a vertical axis extending along the spinal column of the patient.

8. The device of claim 7, wherein said engagement between said first and second branches of said first stop element and said third and fourth branches of said second stop element further provides means for preventing lateral translation of the first vertebra relative to the second vertebra along said transverse axis.

9. The device of claim 8, wherein said engagement between said first and second branches of said first stop element and said third and fourth branches of said second stop element further provides means for facilitating movement of said first and second vertebrae superiorly and inferiorly along said vertical axis and one of posteriorly and anteriorly along said sagittal axis.

10. An intervertebral stabilizing device, comprising:

a first stop element engageable with a first vertebra, said first stop element including laterally spaced first and second branches extending in a first direction therefrom each of said first and second branches having first and second linear portions that are substantially parallel to each other;

a second stop element engageable with a second vertebra, said second stop element including laterally spaced third and fourth branches extending in a second direction therefrom, each of said third and fourth branches having third and fourth linear portions that are substantially parallel to each other, said third and fourth branches of said second stop element being engageable with said first and second branches of said first stop element; and wherein each of said third and fourth branches of said second stop element is positioned between the first and second branches of said first stop element.

11. The device of claim 10, wherein each of said first and second stop elements includes a horizontal branch extending between and laterally spacing the first and second branches and third and fourth branches, respectively.

* * * * *